United States Patent [19]

Nordin et al.

[11] Patent Number: 4,933,075
[45] Date of Patent: Jun. 12, 1990

[54] SORTING METHOD AND APPARATUS USING MICROWAVE PHASE-SHIFT DETECTION

[76] Inventors: Lee Nordin, 168 Pruimbos Avenue, Weltevreden Park, Roodepoort, Transvaal; John D. Salter, 007 Downsview, Patricia Road, Sandown, Sandton, Transvaal, both of South Africa

[21] Appl. No.: 209,846

[22] Filed: Jun. 22, 1988

[30] Foreign Application Priority Data

Jun. 23, 1987 [ZA] South Africa .................. 87/4524
Oct. 5, 1987 [ZA] South Africa .................. 87/7456

[51] Int. Cl.⁵ ........................ B07C 5/34; G01R 27/04
[52] U.S. Cl. .................................... 209/576; 324/629
[58] Field of Search ............. 209/539, 555, 556, 558, 209/576, 586, 644, 639; 324/58 R, 58 A, 58 B, 58.5 R, 585.5 A, 58.5 B

[56] References Cited

U.S. PATENT DOCUMENTS

| | | |
|---|---|---|
| 3,562,642 | 2/1971 | Hochschild . |
| 4,123,702 | 10/1978 | Kinanen et al. ............... 209/576 X |
| 4,407,415 | 10/1983 | Bohme et al. .................. 209/576 X |

FOREIGN PATENT DOCUMENTS

| | | |
|---|---|---|
| 2712600 | 9/1977 | Fed. Rep. of Germany ..... 324/58.5 R |
| 3611926 | 10/1987 | Fed. Rep. of Germany ...... 209/556 |
| 0566551 | 9/1975 | Switzerland ........................ 209/576 |
| 1244585 | 9/1971 | United Kingdom . |
| 1489554 | 10/1977 | United Kingdom . |
| 2048492 | 12/1980 | United Kingdom . |
| 2076146 | 11/1981 | United Kingdom ................ 209/577 |
| 2188727 | 10/1987 | United Kingdom ................ 209/577 |

*Primary Examiner*—Russell D. Stormer
*Assistant Examiner*—Edward M. Wacyra
*Attorney, Agent, or Firm*—Scully, Scott, Murphy & Presser

[57] ABSTRACT

Particles are subjected to incident microwave radiation which induces a certain phase shift in the transmitted or reflected radiation. The transmitted or reflected radiation is detected and a measure of the phase shift is obtained from such detection. The particles are then sorted according to the phase shift which they induce in the incident radiation.

4 Claims, 1 Drawing Sheet

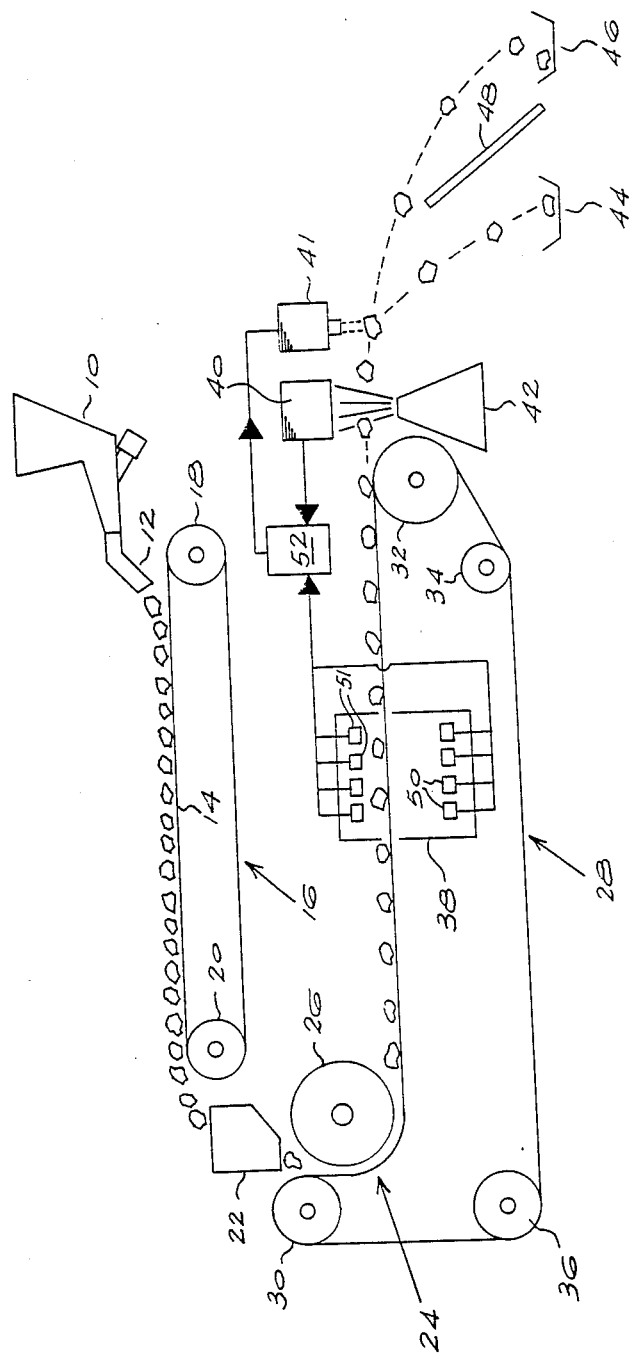

SORTING METHOD AND APPARATUS USING MICROWAVE PHASE-SHIFT DETECTION

BACKGROUND TO THE INVENTION

This invention relates to the sorting of a mass of particles into desired and undesired fractions. In one application of the invention it can be used to sort a mass of ore particles into desired and undesired fractions. One particular application of the invention is in the sorting of diamonds or diamondiferous material from non-diamond or non-diamondiferous material.

SUMMARY OF THE INVENTION

According to the invention there is provided a method of sorting a mass of particulate material into fractions, the method including the steps of subjecting the particles of the mass to incident electromagnetic radiation in the microwave part of the spectrum, analysing the radiation reflected by or transmitted through the particles, and separating from other particles those particles which induce a selected phase-shift characteristic in the radiation.

In one application of the invention it can be used to sort diamond particles or particles of diamondiferous material from non-diamond particles or particles of non-diamondiferous material.

Further according to the invention, there is provided an apparatus for sorting a mass of particulate material into fractions, the apparatus including means for subjecting the particles of the mass to incident electromagnetic radiation in the microwave part of the spectrum, means for detecting radiation which is reflected by or transmitted through the particles, means for analysing the reflected or transmitted radiation and means for separating from other particles those particles which induce a selected phase-shift characteristic in the radiation.

The particles may be subjected to incident microwave radiation while being conveyed in spaced apart relationship on a conveyor belt. Alternatively, the microwave irradiation may take place while the particles are falling in free flight after being projected from, say, a conveyor belt. Preferably also, the reflected or transmitted radiation is detected by means of one or more wave guide antennae. A processor may be used to analyse the signals produced by the or each antenna, such processor also receiving signals from a line scan camera arrangement or other means which detects the size, in particular the thickness, and position of the particles. One or more fluid blast ejectors may be provided which are actuated by the processor and which operate to separate the particles into fractions.

BRIEF DESCRIPTION OF THE DRAWING

The invention will now be described in more detail, by way of example only, with reference to the accompanying drawing which schematically illustrates an apparatus of the invention.

DESCRIPTION OF A PREFERRED EMBODIMENT

The drawing shows a schematic view of a sorting apparatus comprising a vibratory feeder 10 which receives particulate material from a hopper (not illustrated) and which feeds the particles through a discharge chute 12 onto the upper run 14 of a feed belt 16 running around rollers 18 and 20. The feed belt transports the particles to the left in the drawing and discharges them into a feed chute 22 which deposits the particles in an orderly fashion into the nip 24 between a stabiliser wheel 26 and the upper run of a main belt 28 which runs around a series of rollers 30, 32, 34 and 36.

The main belt 28 transports the particles through a detection zone 38, about which more will be said later. The main belt 28 discharges the particles from its upper run in free flight. At an early stage in the free trajectory described by the particles, they are viewed by a line scan camera arrangement 40 mounted opposite a light source 42. Downstream of the line scan camera arrangement 40 is an ejector manifold 41 which issues, through a nozzle or nozzles, a short blast of fluid, typically air, whenever a desired particle passes by. Such particles are ejected from their trajectory by the blast and fall into a bin 44 while other, non-ejected particles continue in free flight into a reject bin 46. A splitter plate 48 is provided between the bins to ensure that efficient separation takes place.

As thus far described, the apparatus is conventional and may typically be an apparatus of the type available from Ore Sorters under the designation "Model 17".

According to the present invention, the detection zone 38 includes a microwave chamber in which is located a series of wave guide antennae, shown schematically at 50, which apply microwave radiation to the chamber and microwave detectors including further wave guide antennae 51 which, in this case, detect the radiation transmitted by the particles as they pass through the chamber.

The wave guide antennae will be designed in a particular case for the known parameters and in accordance with known principles. It should, however, be borne in mind that the antennae should in all cases be smaller in size than the known size of particles which are to be sorted, to ensure that no radiation is able to bypass a particle entirely.

In practice, the particles are arranged into parallel streams on the main belt by the feed system, and wave guide antennae will be provided for each stream on the belt.

The signals detected by the antennae are fed to a processing unit 52. Signals from the line scan camera arrangement; which are indicative of the sizes and locations of the particles discharged from the main belt 28, are also fed to the processing unit 52. The line scan camera arrangement will in particular produce signals indicative of the thicknesses of the particles in a direction parallel to the incident radiation, since the phase shift which is induced in the radiation will be dependent on the thickness of each particle. It should also be noted that suitable means other than a line scan camera arrangement may be used to produce the appropriate signals.

The processing unit 52 analyses all the incoming signals and determines which of the particles have induced a selected phase shift characteristic in the incident radiation in the microwave chamber. In making this determination, the processing unit will make allowance for variations in particle thickness since, as stated previously, phase shift is a function of particle thickness. In practice, the processing unit will be calibrated using particles of known thickness. When such a particle is detected, the processing unit 52 sends, at the appropriate time, a signal to the ejector manifold 41 with the result that a fluid blast is issued and the relevant particle is ejected from its normal trajectory so as to fall into the bin 44.

For other particles which do not exhibit the selected phase shift characteristic, the processing unit 52 sends no signal to the ejector manifold and those particles continue along the normal trajectory so as to fall into the reject bin 46.

EXAMPLES

Example 1

In this example, 2 cm thick samples of kimberlite and gabbro were subjected to microwave radiation at a frequency of 10 GHz and the phase shift characteristics induced in radiation by the samples were monitored. Each sample was subjected to the same test a number of times to produce a range of phase shifts for each sample. The results are tabulated below:

| SAMPLE NO. | PHASE SHIFT (RANGE) |
|---|---|
| GABBRO 1 | 9° to 13.5° |
| GABBRO 2 | 58.5° to 58.5° |
| GABBRO 3 | 45° to 54° |
| KIMBERLITE 1 | 184.5° to 189° |
| KIMBERLITE 2 | 162° to 171° |

Clearly, the kimberlite samples induced a far higher phase shift than the gabbro samples and the phase shift induced in microwave radiation provided a good criterion for subsequent sorting of these materials. The invention therefore finds application in the diamond sorting industry where kimberlite may be diamond-bearing and gabbro is not.

Example 2

This example also illustrates the use of the invention in the diamond sorting industry. In this case, 4 cm thick samples of "boulders", i.e. waste rock and diamond bearing matrix, both types of sample being drawn from the Namaqualand diamond fields in South Africa were subjected to microwave radiation at a frequency of 10 GHz. The boulders induced a phase shift of 90° to 135° in the incident radiation while the diamond-bearing matrix induced a phase shift of 180° to 270° in the radiation. Once again, the induced phase shift was a good criterion for sorting of the samples with the apparatus described previously.

Example 3

This example illustrates the use of the invention in the coal sorting industry where it is desirable to sort coal particles from waste rock. 3 cm thick samples of coal and waste rock mined at the New Denmark Colliery in the Republic of South Africa were subjected to microwave radiation at a frequency of 10 GHz. The phase shift induced in the incident radiation by the coal sample was 280° while that induced in the waste rock sample was 468°, i.e. 360°+108°. Once again, the clear difference in phase shift enabled a sort to be carried out.

Example 4

This example illustrates the use of the invention in yet another industry, namely in the sorting of gold-bearing particulate material from other, waste material. A 3 cm thick sample of Carbon Leader Reef rock was subjected to microwave radiation as were a 3 cm thick sample of Vaal Reef rock and a 6 cm thick sample of waste rock. "Carbon Leader Reef" refers to a rock type known in South Africa to be extremely rich in gold, while "Vaal Reef" refers to a rock type known to be relatively rich, but not quite as rich as the Carbon Leader Reef. The waste rock, on the other hand, was mined from the hanging and footwalls in a gold mine stope.

The Carbon Leader Reef sample induced a phase shift measured to be in excess of 300° while the Vaal Reef sample induced a phase shift of only 100°. The waste rock induced a phase shift of 50° compensation having been made for the greater thickness of the sample. Thus this example indicates that the invention can be used to sort rock particles mined in a gold mine not only into gold-bearing and non gold-bearing fractions but also into different grades. The microwave frequency used in each case will depend upon the nature of the materials which are to be sorted. In practice, that frequency which is known to induce a particular phase shift in radiation incident on a desired material or on a sample containing that material will be used.

We claim:

1. A method of sorting a mass of particulate ore into fractions, the method including the steps of subjecting the particles of the mass to incident electromagnetic radiation in the microwave part of the spectrum, analysing the phase shift in the radiation reflected by or transmitted through the particles, relative to the incident radiation, and separating from other particles those particles which induce a selected phase-shift characteristic in the radiation.

2. A method according to claim 1, wherein diamond particles or particles of diamondiferous ore are sorted from non-diamond particles or particles of non-diamondiferous ore.

3. A method according to claim 2, wherein particles of kimberlite are sorted from particles of gabbro.

4. An apparatus for sorting a mass of particulate ore into fractions, the apparatus including means for subjecting the particles of the mass to incident electromagnetic radiation in the microwave part of the spectrum, means for detecting radiation which is reflected by or transmitted through the particles, means for analysing the phase shift in the reflected or transmitted radiation relative to the incident radiation and means for separating from other particles those particles which induce a selected phase-shift characteristic in the radiation.

* * * * *